(12) United States Patent
Zwirkoski et al.

(10) Patent No.: US 6,200,316 B1
(45) Date of Patent: Mar. 13, 2001

(54) INTRAMEDULLARY NAIL DISTAL TARGETING DEVICE

(76) Inventors: Paul A. Zwirkoski, 121 W. North St., Suite 8, Brighton, MI (US) 48116; Owen F. M. Donohoe, 6265 Arapahoe, Shawnee Mission, KS (US) 66216

( * ) Notice: Subject to any disclaimer, the term of this patent is extended or adjusted under 35 U.S.C. 154(b) by 0 days.

(21) Appl. No.: 09/306,639

(22) Filed: May 7, 1999

(51) Int. Cl.[7] .................................................. A61B 17/56
(52) U.S. Cl. ................................ 606/62; 606/60; 606/130
(58) Field of Search ........................... 606/62, 54, 56, 606/60, 61, 65, 67, 72, 130

(56) References Cited

U.S. PATENT DOCUMENTS

| | | | |
|---|---|---|---|
| 4,418,422 | 11/1983 | Richter et al. | 378/205 |
| 4,667,664 | 5/1987 | Taylor et al. | 128/92 |
| 4,803,976 | 2/1989 | Frigg et al. | 128/92 |
| 4,976,713 | * 12/1990 | Landanger et al. | 606/62 |
| 5,013,317 | 5/1991 | Cole et al. | 606/96 |
| 5,540,691 | 7/1996 | Elstrom et al. | 606/64 |
| 5,746,741 | * 5/1998 | Kraus et al. | 606/54 |
| 5,772,594 | 6/1998 | Barrick | 600/407 |
| 5,776,143 | * 7/1998 | Adams | 606/130 |

FOREIGN PATENT DOCUMENTS

2213066 * 8/1989 (GB) .................................. 606/130

* cited by examiner

Primary Examiner—Michael Buiz
Assistant Examiner—Lien Ngo
(74) Attorney, Agent, or Firm—Charles W. Chandler

(57) ABSTRACT

A targeting device for aligning a viewing device between a radiation source and a radiation receiver along an axis that passes through the fastener-receiving hole in an intramedullary nail or rod. The targeting device is aligned such that the viewing axis coincides with the radiation axis, which in turn coincides with an axis that passes through the fastener-receiving hole, to prepare to insert a fastener for attaching the nail to a bone in which the nail is implanted.

The apparatus and method reduces the procedural time associated with the accurate placement of screws or pins into orthopedic hardware, such as the distal locking holes of intramedullary nails/rods in long bone fractures.

18 Claims, 16 Drawing Sheets

INTRAMEDULLARY NAIL DISTAL TARGETING DEVICE

BACKGROUND OF THE INVENTION

This invention relates to a targeting device for inserting a fastener into the distal end of a femoral nail.

Intramedullary nailing has become one of the most effective methods for stabilizing orthopedic shaft fractures. Designs that interlock bone and nail have expanded the indications for Intramedullary Nailing (IM) considerably.

These interlocking nail designs, while generally successful, are associated with some difficulties, such as an inability to localize the distal locking holes and missed locking, that result in prolonged operating and fluoroscopy time. In addition, since no reliable distal targeting device has been developed, most surgeons are exposed to considerable radiation during distal screw insertion.

The problem of properly inserting the distal locking screws from outside the limb of the patient into corresponding screw holes in the nail is a challenging one. The proper positioning of such locking screws or pins is typically the most time-consuming and difficult portion of the overall nail implantation procedure.

A number of different approaches have been taken in attempting to find an effective, safe, simple, and rapid method. These include U.S. Pat. No. 5,772,594 issued Jun. 30, 1998, to Earl F. Barrick for "Fluoroscopic Image Guided Orthopaedic Surgery System with Intraoperative Registration"; U.S. Pat. No. 5,540,691 issued Jul. 30, 1996 to John A. Elstrom and Peter Elstrom for "Optical Distal Targeting method for an Intramedullary Nail"; U.S. Pat. No. 5,013,317 issued May 7, 1991 to J. Dean Cole and A. Glenn Durham for "Medical Drill Assembly Transparent to X-rays and Targeting Drill Bit"; U.S. Pat. No. 4,976,713 issued Dec. 11, 1990 to Joël Landanger and Jean P. Michel for "Aiming Device to Position at Least One Fixing Component of the Centromedullar Nail Type, Through an Implant"; U.S. Pat. No. 4,803,976 issued Feb. 14, 1989 to Robert Frigg et al. for "Sighting Instrument"; U.S. Pat. No. 4,667,664 issued May 26, 1987 to Harold S. Taylor and John C. Taylor for "Blind Hole Targeting Device for Orthopedic Surgery"; and U.S. Pat. No. 4,418,422 issued Nov. 29, 1983 to Karl M. Richter et al. for "Aiming Device for Setting Nails in Bones".

Typically, a C-arm x-ray provides an image for the surgeon to view the locking holes in the nail. It is necessary to precisely align the axis of the targeting device with the axis of the locking holes after the radiation axis of the x-ray has been aligned with the locking holes. Usually prior art viewing devices employ a carriage mounted on a mounting plate to move the targeting device in at least 2 degrees of freedom, in planes generally parallel to the nail to locate the axis of the targeting device with the locking holes. The viewing axis of the targeting device must be precisely located to coincide with the axis of the locking holes.

SUMMARY OF THE INVENTION

The broad purpose of the present invention is to provide an improved method and device for aligning the axis of a fastener insertion (locking) hole with the axis of the holes in the orthopedic hardware, such as the distal end of a femoral nail.

In the preferred embodiment, a mounting plate is strapped on the user's limb adjacent the distal end of the nail. The targeting device is slidably supported on rods disposed in a plane generally parallel to the implanted nail. A ball and socket joint supports the targeting device so that it can be rotated with the aid of a radiation source that is aligned with the locking holes until the viewing axis coincides with the axis of the locking holes. The bone is drilled and then the fastener is inserted both through the targeting device and the nail.

The intent/purpose of the invention is as follows: to improve the reliability/accuracy of alignment; to eliminate surgeon exposure to the associated radiation; to be inherently easy to use; and to improve the associated procedural time of surgery.

The principle features of the invention include: a one step adjustment for each the x and y directions; a ball and socket joint supporting the targeting device for spherical adjustment such that the viewing axis coincides with the axis of the distal holes of the nail; hands-free operation during x-ray; and a tourniquet design for secure attachment to the patient.

The procedure and apparatus may be used in other long bone fractures, such as a humeral bone, and for use either with a solid or hollow nail.

Still further objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which.

DESCRIPTION OF THE PREFERRED EMBODIMENT

Figure 1:
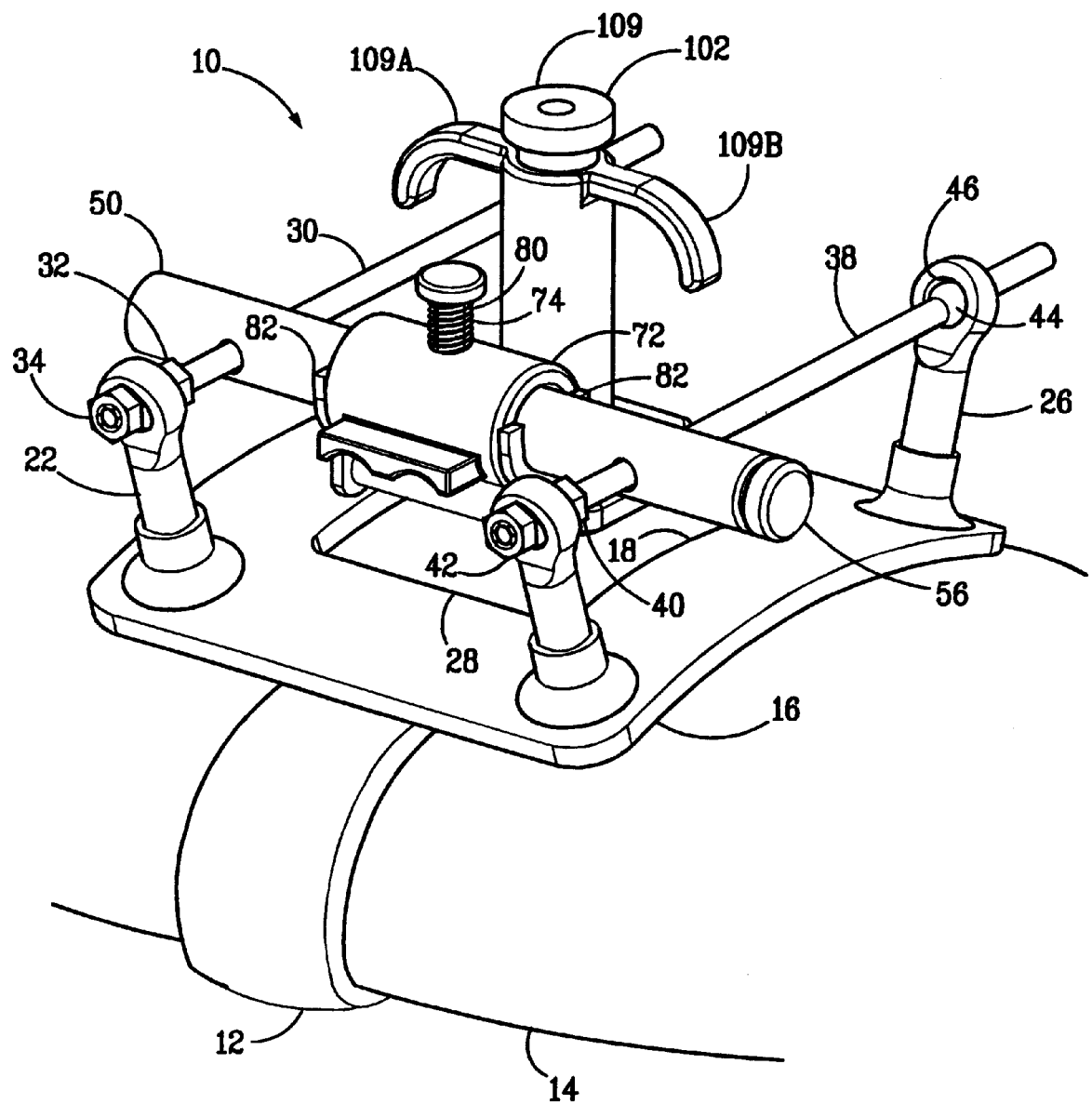
FIG. 1 illustrates a targeting device embodying the invention.

Referring to the drawings, FIG. 1 illustrates a preferred targeting device, generally indicated at 10, attached by strap means 12 to the leg 14 of a patient, in a relatively fixed position with respect to the leg. Targeting device 10 includes a curved, rectangular, rigid plate-like base 16. The base has a central, rectangular opening 18 disposed adjacent the distal end of a conventional hollow femoral nail 20 implanted in a fractured femur 21, illustrated in FIG. 5.

The base has four upright apertured posts 22, 24, 26 and 28 adjacent the four corners of the plate. Straight guide rod 30 is supported in the apertures of posts 22 and 24 above the base plate on one side of opening 18. One end of the guide rod is threaded to receive a pair of locking nuts 32 and 34 for rigidly fastening the guide rod to the upper end of post 22. The opposite end of guide rod 30 has a ball joint 35 mounted in a ball-shaped socket 36 at the upper end of port 24.

A second straight guide rod 38 is received through the apertures of posts 26 and 28. One end of guide rod 38 is threaded to receive a pair of fasteners 40 and 42. The opposite end of guide rod 38 has a ball-joint 44 received in a ball-shaped socket 46 at the upper end of post 26 in such a manner that guide rod 38 is parallel to guide rod 30.

Both of the guide rods are disposed in an imaginary plane that is generally parallel to the longitudinal axis of femoral nail 20.

Figure 2:
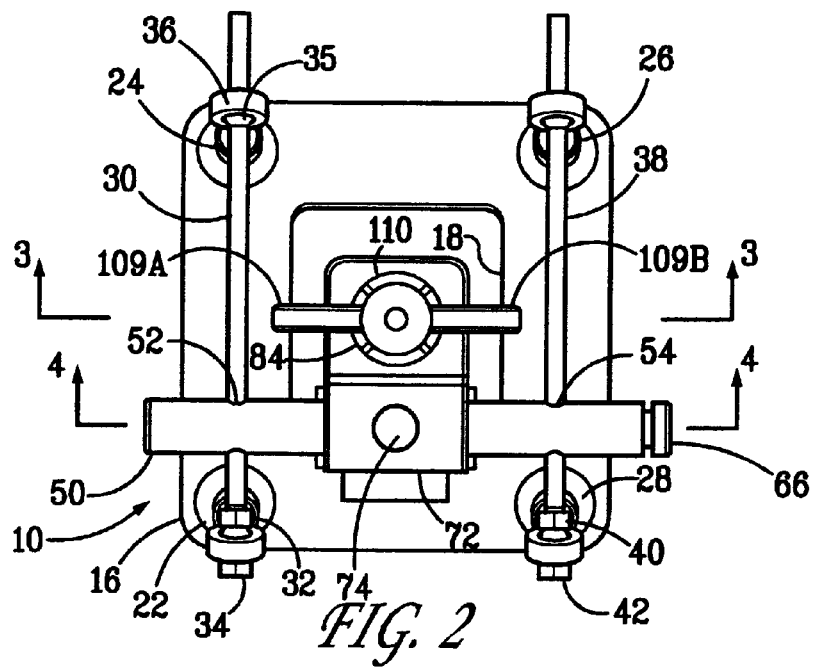
FIG. 2 is a plan view of the targeting device of FIG. 1.
Figure 4:
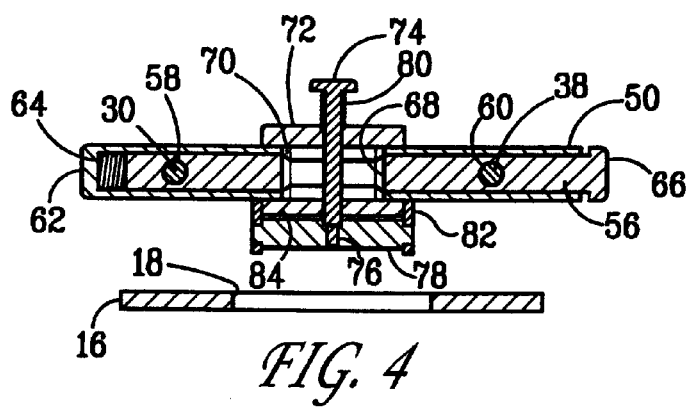
FIG. 4 is a view as seen along the lines 4—4 of FIG. 2.

Referring to FIGS. 2 and 4, a tubular linear guide sleeve 50 has a pair of opening means 52 and 54 mounted on guide rods 30 and 38, at right angles to the parallel axis of the two guide rods.

As best shown in FIG. 4, a pin 56 is telescopically received in sleeve 50. The pin has a pair of opening means 58 and 60 aligned with the openings in the guide sleeve to slidably receive guide rods 30 and 38. One end of the sleeve is closed at 62 to provide a housing for a spring-bias member 64 which biases pin 56 and the sleeve in opposite directions to frictionally engage guide rods 30 and 38 in an adjustable releasable position.

The pin has an enlarged head 66 having a diameter larger than the open end of the sleeve and normally spaced from the sleeve a sufficient distance so that the user can release the pin and the sleeve from their frictional engagement on the two guide rods by pushing head 66 toward spring 64. The user can then precisely locate the position of the sleeve on the two guide rods.

Referring to FIG. 4, pin 56 has a slot 68 aligned with a slot 70 in sleeve 50. A locking sleeve 72 is frictionally slidably mounted on the guide sleeve over slot 68 and slot 70. A plunger 74 is mounted in slots 68 and 70. The plunger has a lower threaded end 76 received in a cross bar 78. A spring 80 is mounted between the head of the plunger and the locking sleeve to bias the plunger and cross bar 78 toward the locking sleeve.

Cross bar 78 carries a pair of Y-shaped supports 82a and 82b which cradle sleeve 50. Plunger 74 is pushed downwardly as viewed in FIG. 4, with supports 82a and 82b to move it to an adjusted position along the length of slot 68, and then released to permit supports 82a and 82b to frictionally lock the locking sleeve in an adjusted position along sleeve 50.

Figure 3:
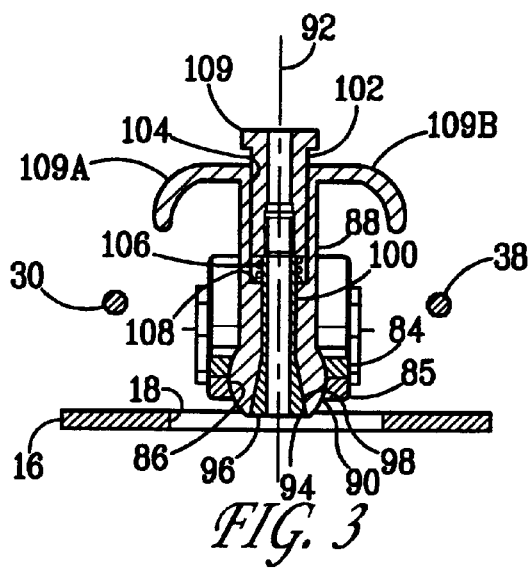
FIG. 3 is a view as seen along lines 3—3 of FIG. 2.

Locking sleeve 72 supports an L-shaped cradle 84 as illustrated in FIGS. 3 and 4. The cradle and a lower plate 85 are connected together by fasteners, not shown, to define a partially spherical socket 86 suspended above opening 18.

Still referring to FIG. 3, a tubular target housing 88 has an integral ball-shaped, slotted, expandable joint 90 frictionally received in socket 86 so that longitudinal target axis 92 can be rotated to an adjusted angle with respect to the nail. Axis 92 passes through the center of rotation of joint 90.

Joint 90 has an internally tapered opening 94. An elongated clamping element 96 has an externally tapered surface 98 that is complementary to tapered opening 94, and a cylindrical midsection 100 that is slidably mounted in a cylindrical extension of tapered opening 94. Clamping element 96 is shown in FIG. 3 clamping joint 90 in socket 86.

A plunger 102 is slidably mounted in an opening 104 of housing 88. A spring 106 is disposed at the lower end of plunger 102. The spring is retained between the plunger and an internal shoulder 108 in housing 88 in such a position that by pushing down on head 109 of the plunger, clamping element 96 is lowered in tapered opening 94 to release the joint. The joint can then be rotated to adjust the angle of the target axis with respect to the nail locking openings.

The outer end of housing 88 has a pair of gripping fingers 109A and 109B that permit the user to depress plunger 102 when he is adjusting target axis 92 with respect to the nail.

Although this embodiment illustrates an internal clamping element, a solid ball with a viewing hole, and an outside clamping means could also be used.

Plunger 102 and clamping element 96 define an opening 103, which passes through the ball joint and has a sufficient diameter to receive a sleeve (not shown).

Figure 5:
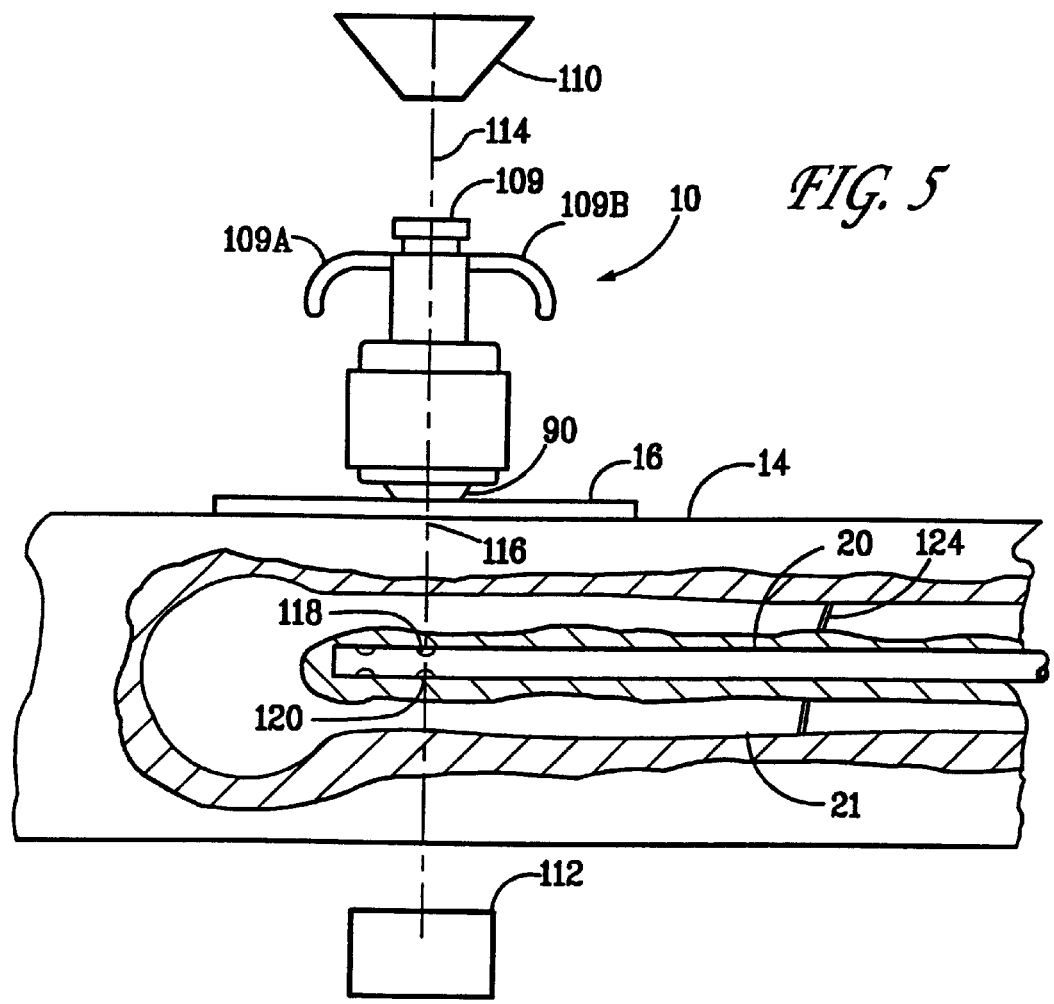
FIG. 5 is a fragmentary view illustrating how the targeting device is aligned with the holes in the nail.
Figure 6:
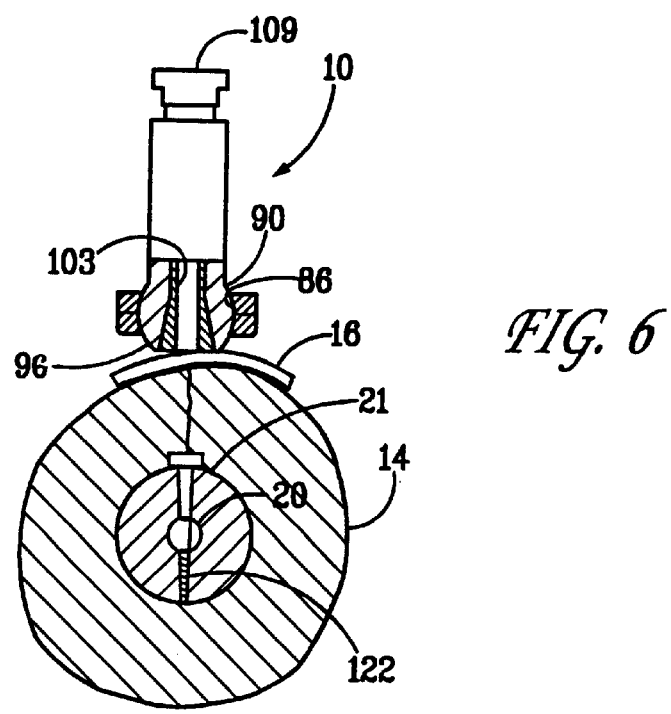
FIG. 6 is a fragmentary view similar to FIG. 5 but at right angles thereto.

Referring to FIGS. 5 and 6, in use, the patient's leg 14 is mounted between the radiation discharge end 110 and the radiation-receiving end 112 of a conventional C-shaped x-ray device. The x-ray device passes radiation along a radiation axis 114 through opening 103. The position of the radiation device is adjusted until radiation axis 114 coincides with the axis 116 of a pair of aligned nail locking holes 118 and 120 in the wall of nail 20. When the radiation axis 114 is aligned with hole axis 116, the user can view the position of the locking holes 118 and 120 through a conventional x-ray image screen, not shown.

He then moves the target housing 88 along guide rods 30 and 38, and along guide sleeve 50 until the target housing is proximate nail locking holes 118 and 120. He rotates the target housing and the ball joint in socket 86 to adjust the angle of target axis 92 until it is aligned with hole axis 116.

He then inserts a drill, not shown, through the sleeve in the target housing along axis 92 to drill holes in the bone that are aligned with the locking holes. He removes the drill and sleeve and then inserts a fastener into the target housing, into the holes in the bone and the nail, and screws the nail to the bone.

As is well known, this procedure is typically accomplished in order to permit a fracture 124 to set when the bone segments are aligned on the nail.

FIGS. 7 through 12 illustrate a preferred targeting device 200. Targeting device 200 is mounted in a fixed position on the patient's leg and includes a frame 202. The frame includes a pair of end members 204 and 206 connected together by a pair of upper parallel frame rods 208 and 210, and a lower pair of strapping rods 212 and 214.

Frame 202 also has a cross member 216 at the upper end of the end piece 204, and an identical cross member 218 at the upper end of end piece 206.

Figure 9:
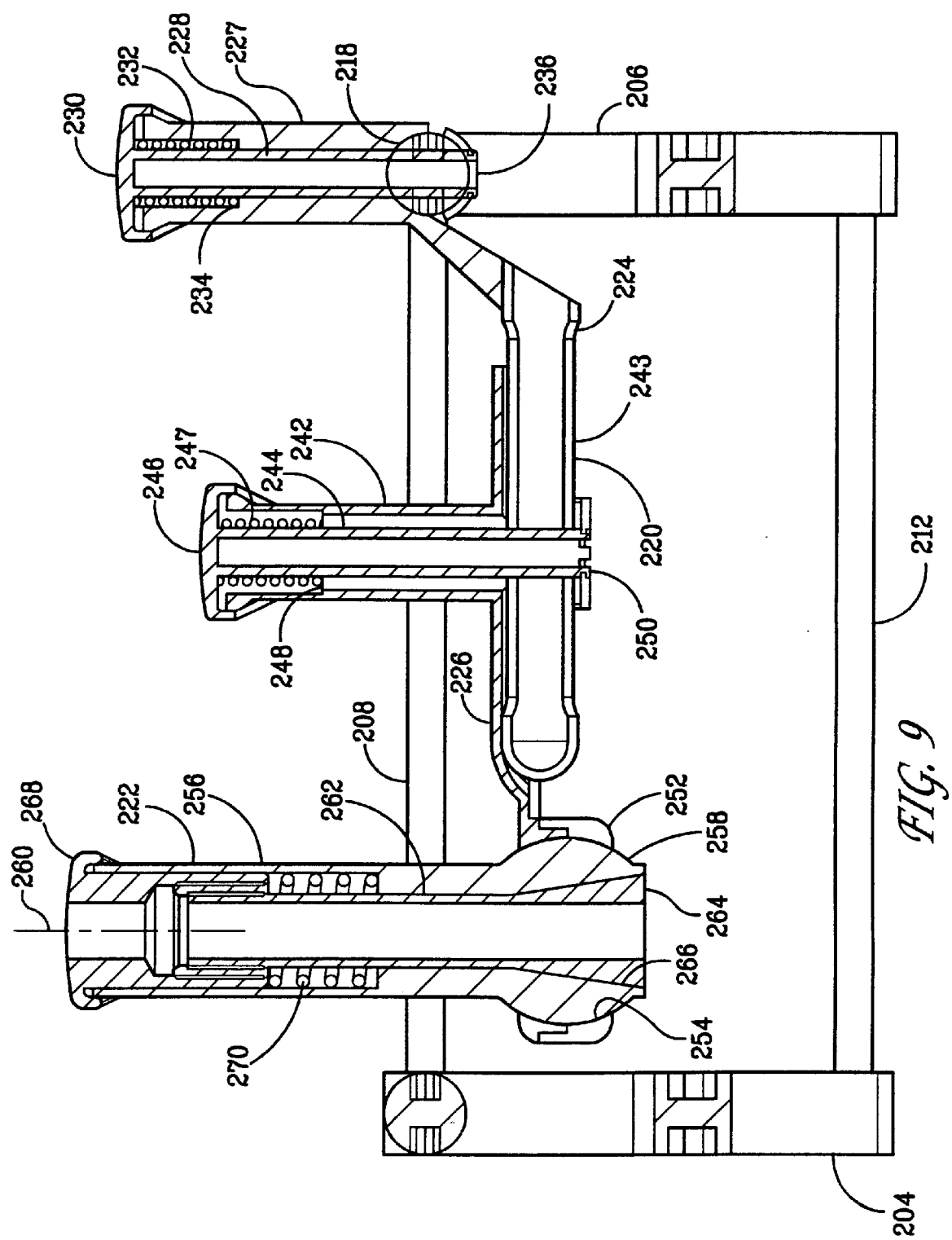
FIG. 9 is a sectional view as seen along lines 9—9 of FIG. 8.
Figure 10:
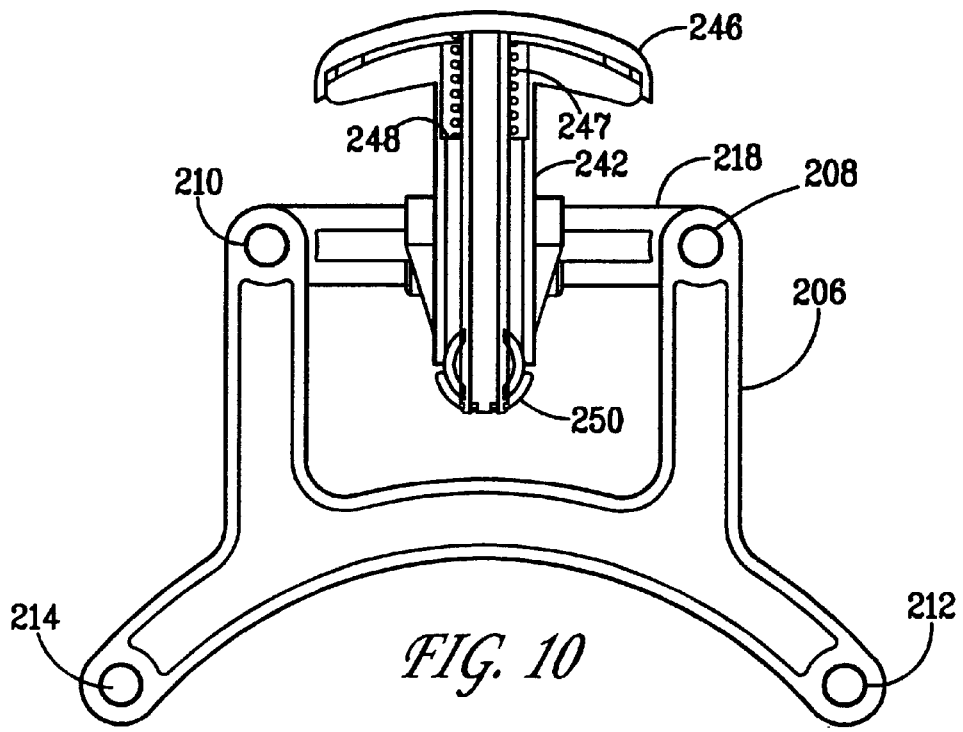
FIG. 10 is a sectional view as seen along lines 10—10 of FIG. 8.

Referring to FIG. 9, an elongated telescopic support 220 has one end mounted on cross member 218. The opposite end of the telescopic support carries a targeting device 222, supported in a cantilever fashion with respect to cross member 218.

Support 220 comprises a pair of telescopically engaged tubular members 224 and 226 so that the suspended end of support 220 can be moved either toward or away from cross member 218 in order to precisely locate the targeting device with respect to the nail.

Tubular member 224 has an upright hollow support 227. A vertical locking pin 228 is mounted in support 227. A push button 230 is carried on the upper end of pin 228. A coil spring 232 is mounted between push button 230 and a shoulder 234 inside support 227 so that the locking pin can be pushed downwardly to release a locking shoe 236 that engages the bottom surface of cross member 218. When the telescopic support is properly oriented, locking pin 228 is released to lock the targeting device in a selected position along cross member 218.

Referring to FIG. 9, inner tubular member 226 supports a tubular vertical housing 242. A locking pin 244 is slidably disposed in housing 242 and through a slot 243 in support 220. A push button 246 is carried at the upper end of locking pin 244. A spring 247 is mounted beneath push button 246 and a shoulder 248 to bias the pin upwardly. The lower end of the locking pin has a locking shoe 250 that frictionally engages support 220 so that when the push button is pushed downwardly, the two tubes can be longitudinally moved with respect to one another in order to increase the overall suspended length of the support.

Figure 7:
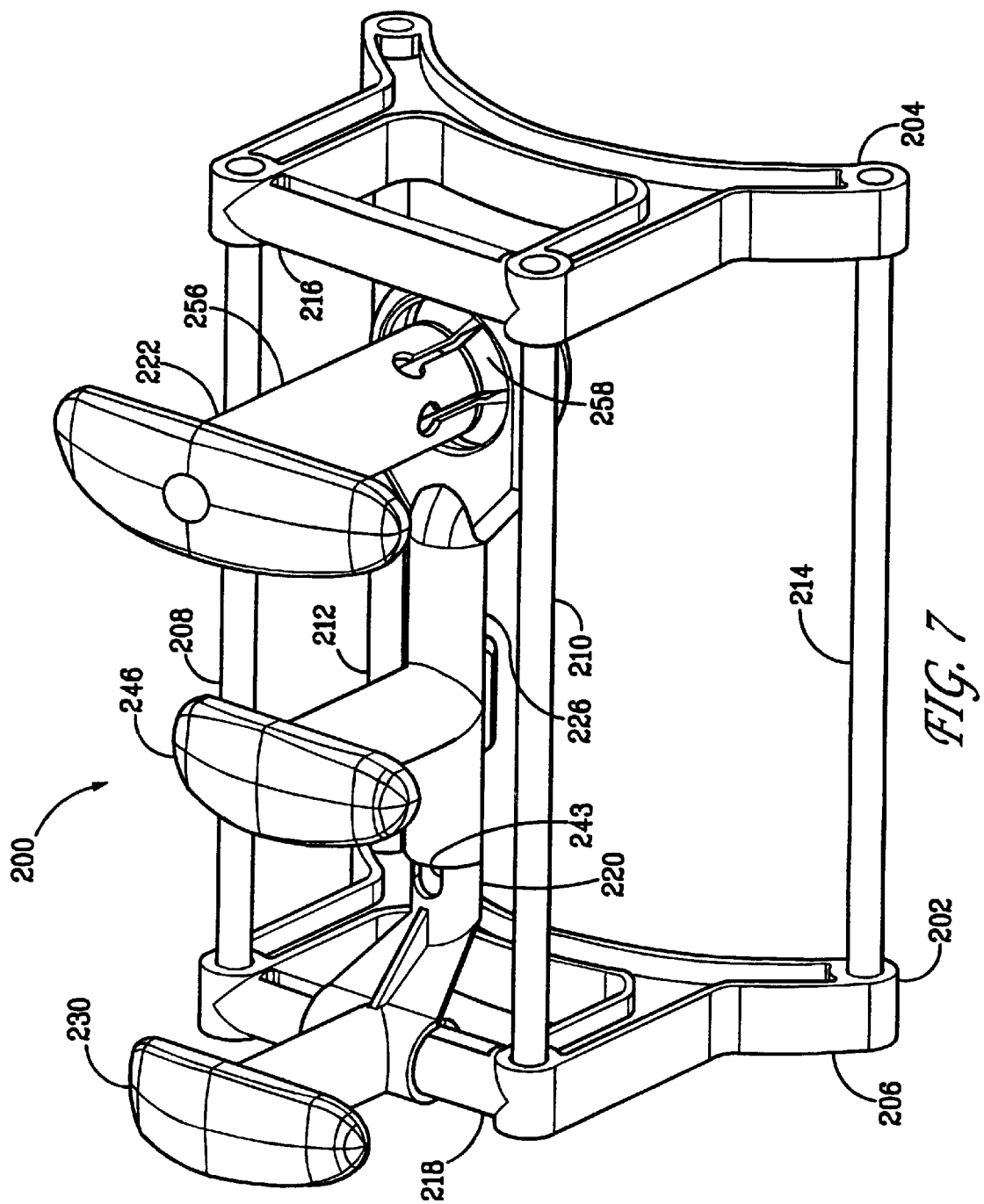
FIG. 7 is a perspective view of another targeting device embodying the invention.
Figure 8:
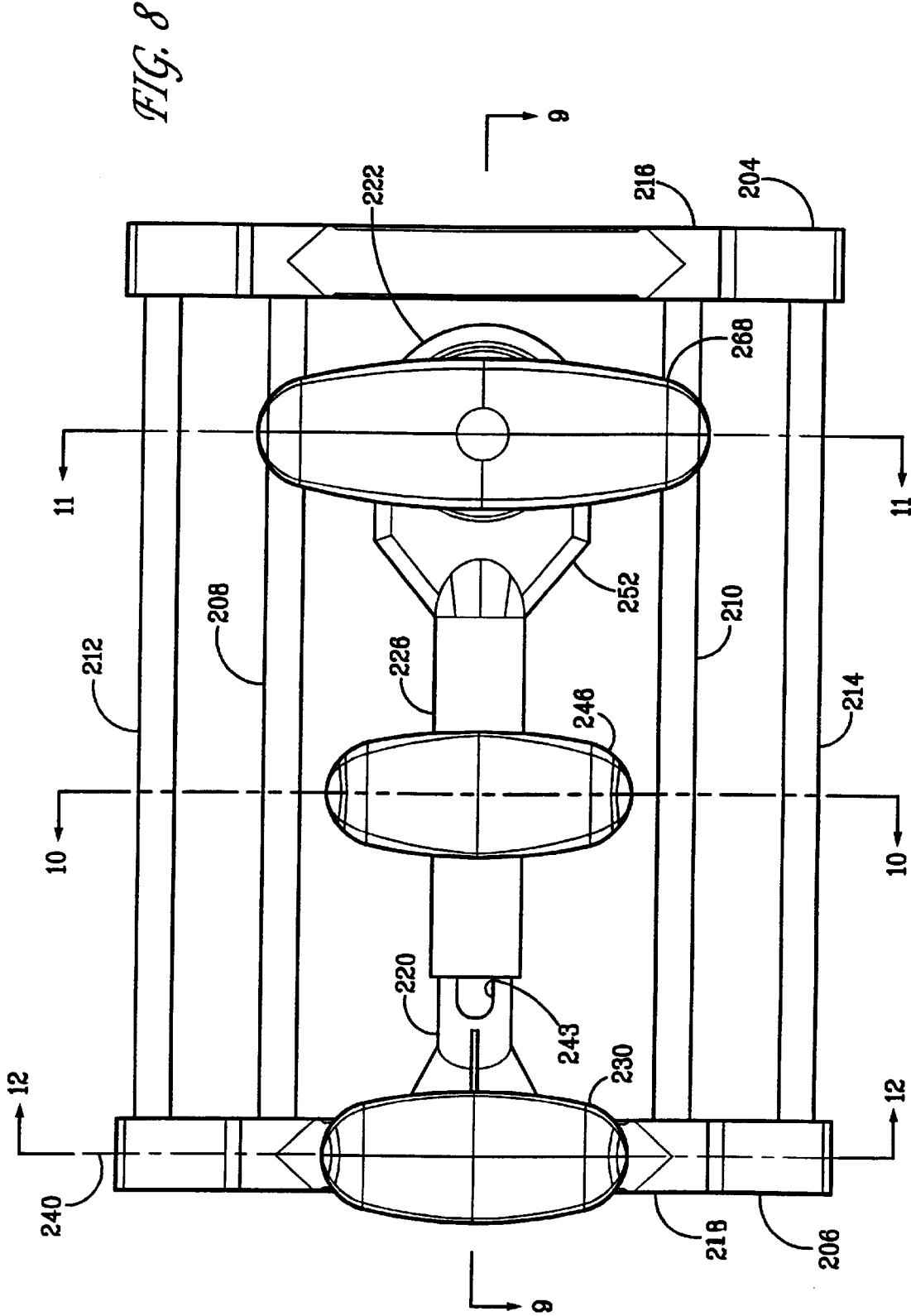
FIG. 8 is a plan view of the targeting device of FIG. 7.
Figure 11:
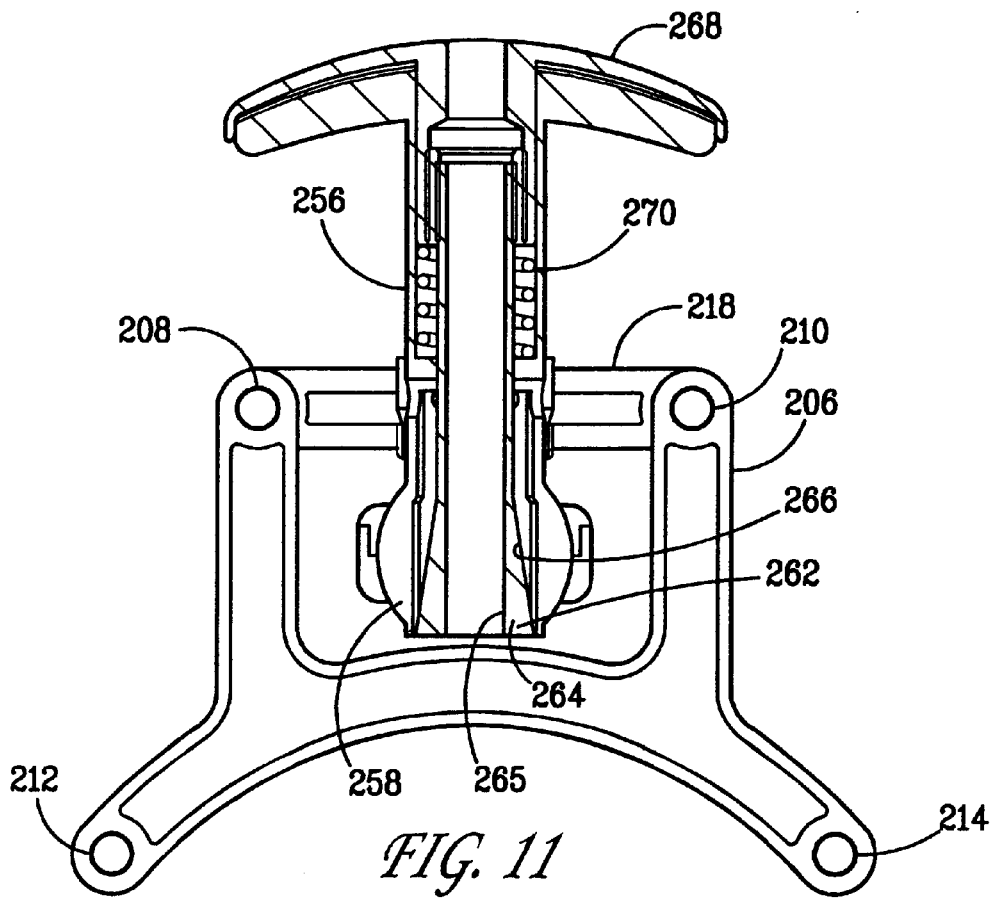
FIG. 11 is a view as seen along lines 11—11 of FIG. 8.
Figure 12:
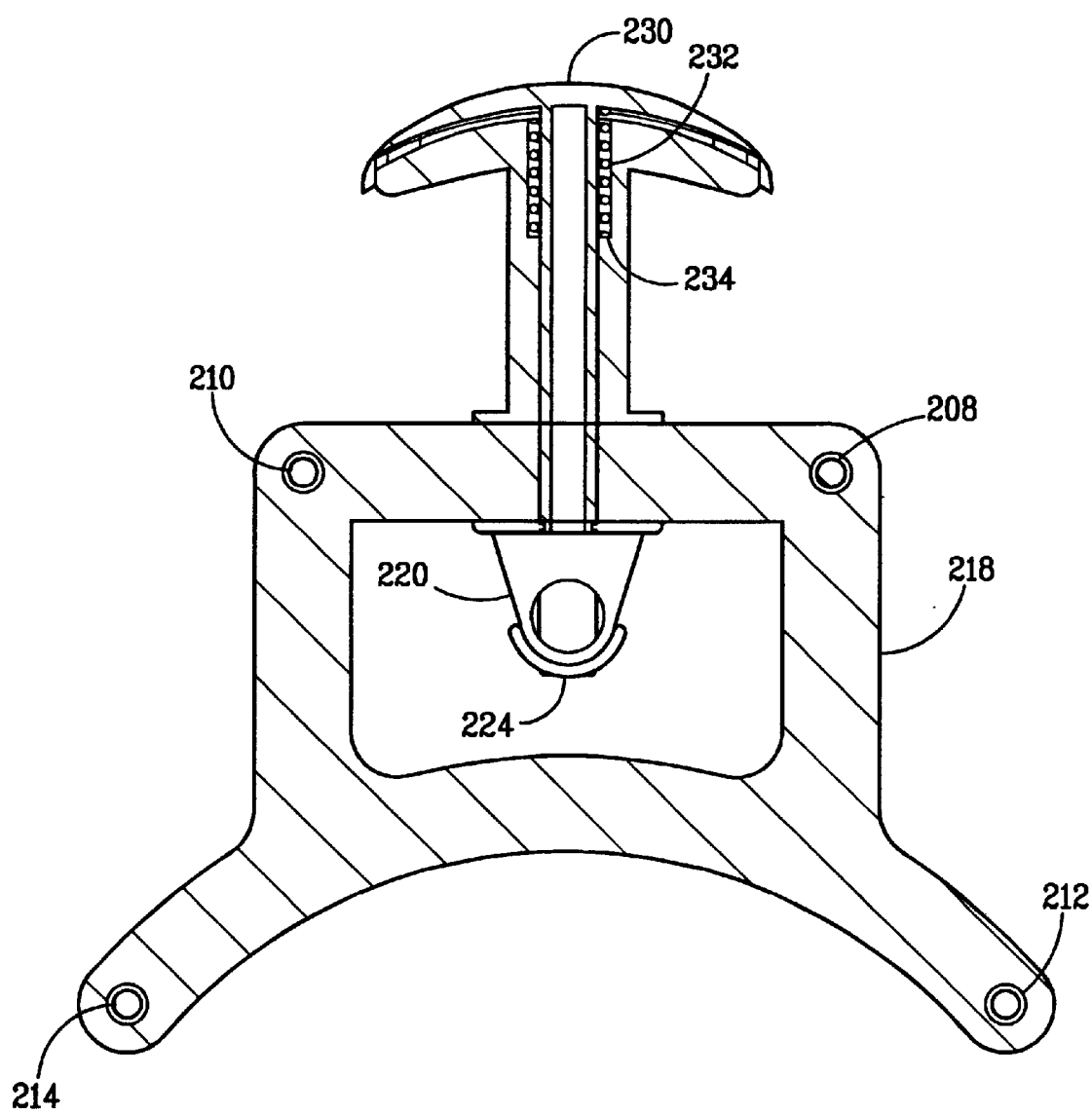
FIG. 12 is a view as seen along lines 12—12 of FIG. 8.

Referring to FIGS. 7 and 11, the extreme suspended end of the telescopic support has a socket 252 with an internal partially spherical bearing socket 254. The targeting device includes a viewing tube 256 having a partially spherical, split, expandable ball 258 received inside socket 254 so that the targeting device can be swung in an orbit about a targeting axis 260 to precisely align axis 260 with the nail locking openings.

An elongated locking tube 262 has a lower tapered end 264 received in a tapered opening 266 of expandable ball 258. A push button 268 is carried at the upper end of the locking tube to push it downwardly from tapered opening 266 thereby freeing ball 258 to permit rotation of the targeting device in socket 252. When the push button is released, a spring 270 biases the locking tube upwardly so tapered end 264 locks the ball in the socket.

Tube 262 and push button 268 also define a through opening 265 for receiving a drill, a drill sleeve and then a fastener.

In use, the targeting device is adjusted in a similar manner to the embodiment of FIGS. 1 through 6, that is, the targeting device is extended along the axis of the telescopic support and adjusted along cross member 218 to align the targeting axis 260 with the nail locking holes.

A sleeve, not shown, is inserted in locking tube 262. A drill is inserted in the sleeve in the conventional manner to drill a hole in the patient's femur. The drill and sleeve are then removed and a threaded fastener inserted through opening 265 into the drilled hole to attach the femur to the nail.

Figure 13:
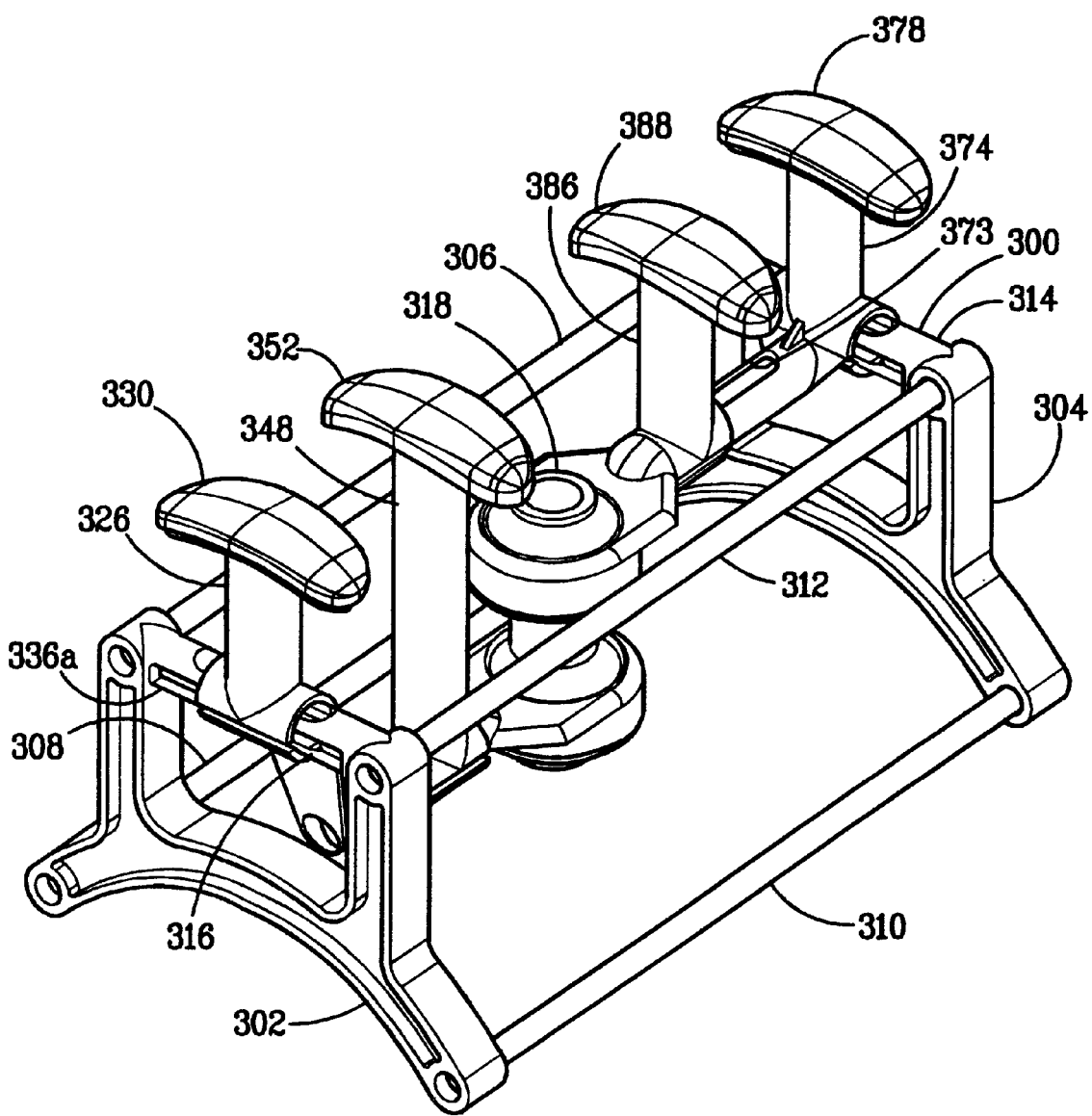
FIG. 13 is a perspective view of still a further embodiment of the invention employing a double ball and socket joint.
Figure 14:
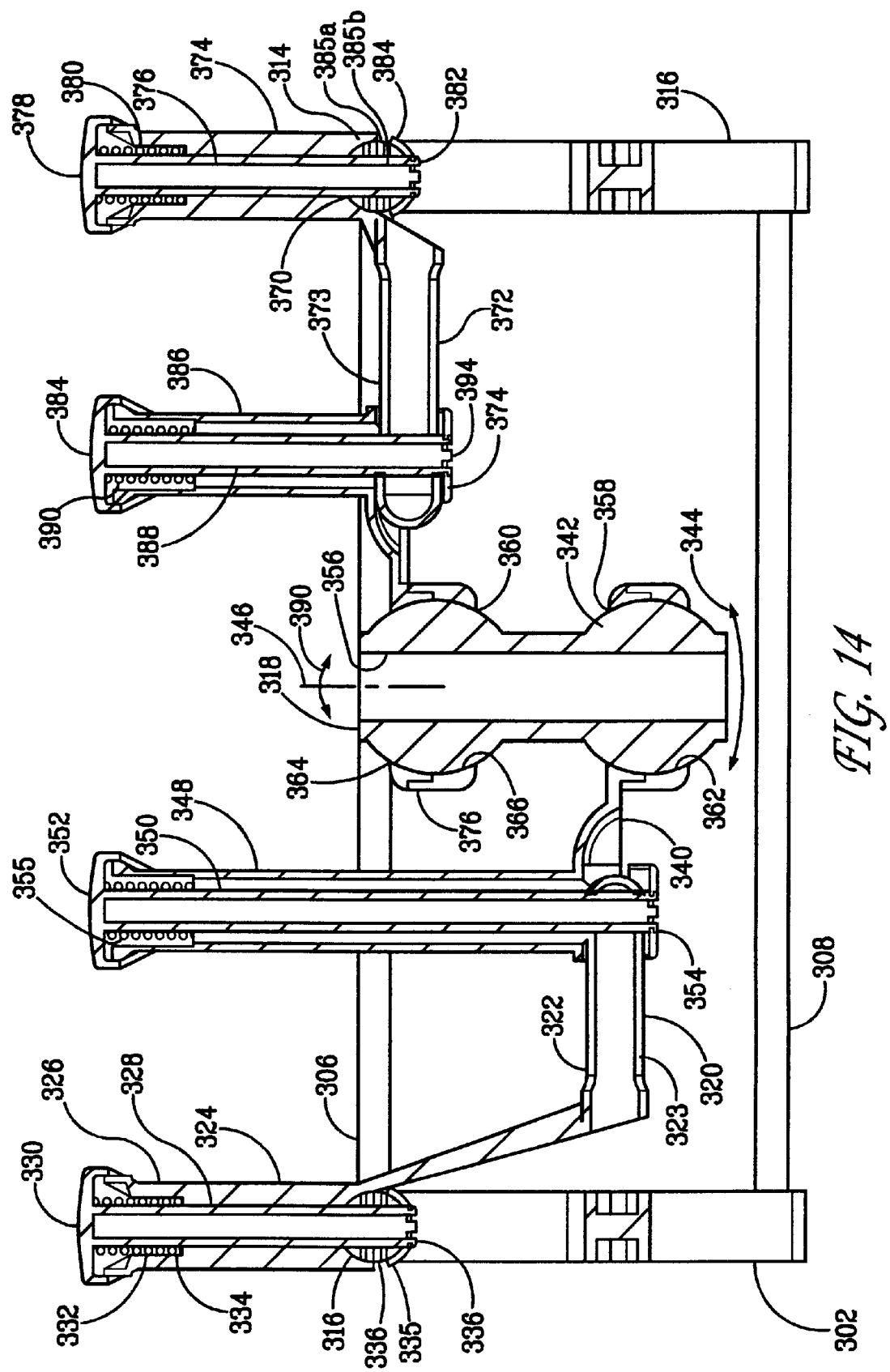
FIG. 14 is a longitudinal sectional view of the targeting device of FIG. 13.

FIGS. 13 and 14 illustrate another targeting device 300 illustrating the invention. Targeting device 300 comprises a frame end piece 302 and frame end piece 304 connected by four parallel rods 306, 308, 310 and 312. Rods 308 and 310 provide means for strapping the targeting device on the user's limb in manner that will be presently described.

The frame end pieces carry a pair of tubular parallel slotted cross rods 314 and 316 at their respective ends.

A targeting device 318 is suspended from tubular support 320 cross rod 314. Support 320 includes a tubular section 322 having a slot 323 and a leg 324 rotatably mounted on cross rod 316. Leg 324 can be adjusted along cross rod 314.

Leg 324 includes a tubular housing 326. A locking pin 328 is telescopically received in housing 326. A push button 330 is carried on the upper end of locking pin 328. A spring 332 mounted between push button 330 and a shoulder 334 in the housing to bias the locking pin upwardly to a locking position. The locking pin can be pushed downwardly to release a locking shoe 335 from the cross rod to slide the housing along the cross rod. A pin 336 in slot 336a in the cross rod prevents housing 326 from rotating about the cross rod.

The inner end of support 320 is rotatably connected to a support section 340 to permit the lower portion of targeting body 342 to be swung in the direction of arrows 344 to adjust the angle of viewing axis 346 of the targeting body.

A locking tube 348, carried on tubular support 320, has a locking pin 350 which is pushed downwardly by a push button 352 to disengage a locking shoe 354 from support 320. The push button is then released, and biased upwardly by a spring 355 to cause the shoe to frictionally engage support 320 to lock the lower end of locking tube 348 in position.

Targeting body 342, as best seen in FIG. 14, has a generally longitudinal viewing bore 356 with a diameter sufficient to receive a sleeve and drill for forming a hole in the patient's femur. Body 342 has a lower, partially spherical exterior annular surface 358 and an upper partially spherical annular surface 360. Lower spherical surface 358 is mounted in a spherical socket 362 suspended from the lower end of locking tube 348.

A second support leg 370 is slidably mounted on cross rod 314, and carries a support tube 372 having a slot 373. A locking tube 374 is attached to support tube 372 and carries a locking pin 376 with a push button 378. Pin 376 is received in the slot of cross rod 314. Push button 378 is depressed to push the locking pin downwardly against the bias of a spring 380 to release a locking shoe 382 carried on the lower end of the pin and engaged with cross rod 314. Leg 370 is then slid along cross rod 314. When the targeting body is located in an appropriate position, the push button is released so that locking shoe 382 locks support leg 370 in position.

Leg 370 has an elbow 384 rotatably mounted on cross rod 314. A pin 385a is carried by the elbow and received in slot 385b to prevent rotation of support tube 372 about the cross rod.

A locking tube 386 is carried on support tube 372 and has a locking pin 388 with a push button 390 for pushing the locking pin downwardly through locking tube 386 to release shoe 392. Locking pin 388 extends through slot 373 in tube 372. When the angle of the viewing axis has been properly located, the push button is released and pushed upwardly by a spring 394 to lock the upper half of the targeting body in position.

When the targeting device has been locked in position, the process for drilling a hole in the femur and then inserting the fastener through viewing bore 356 is achieved in the manner described with reference to the other embodiments of the invention.

Figure 15:
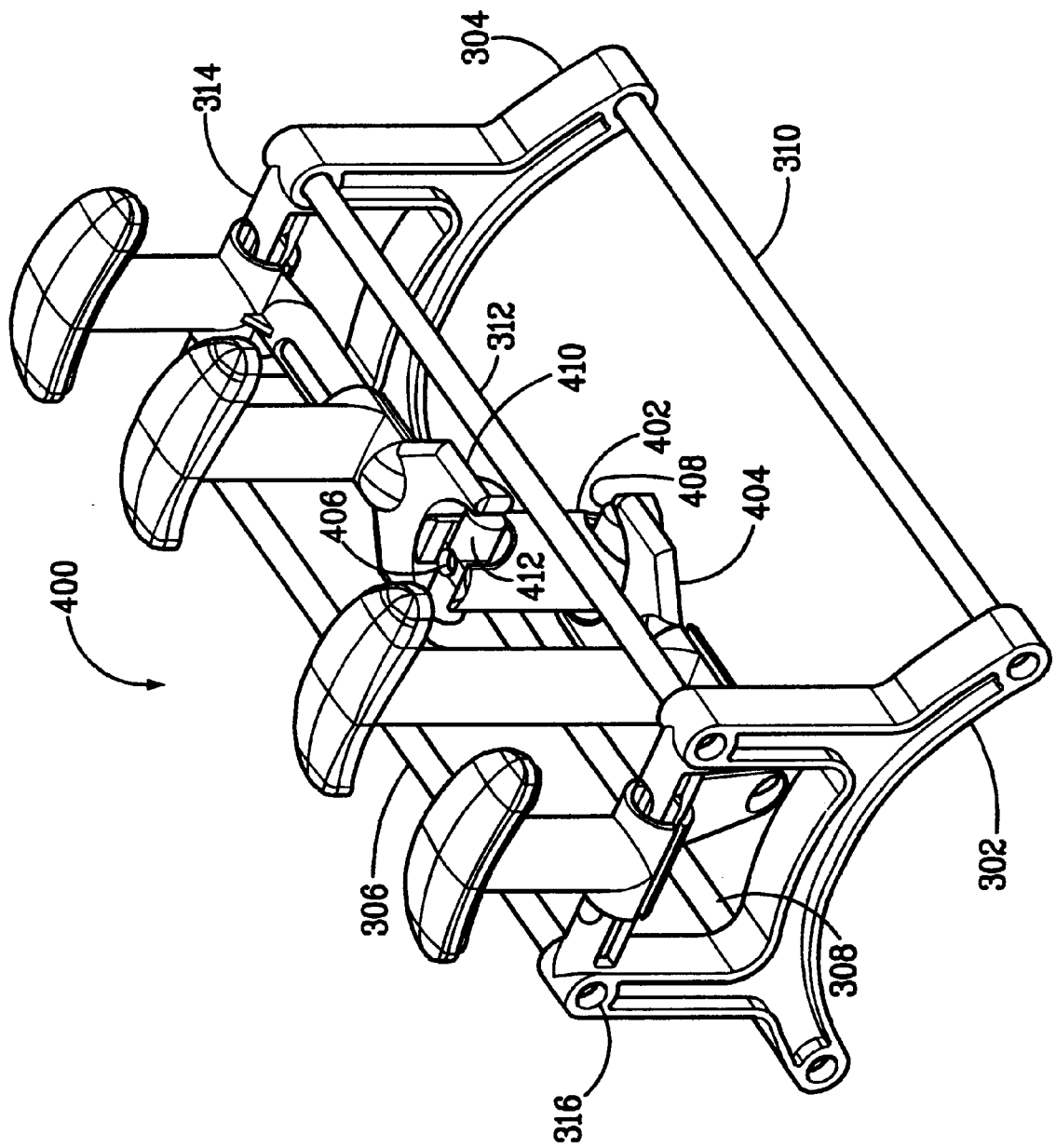
FIG. 15 is a perspective view of still another embodiment of the invention employing a universal joint.
Figure 16:
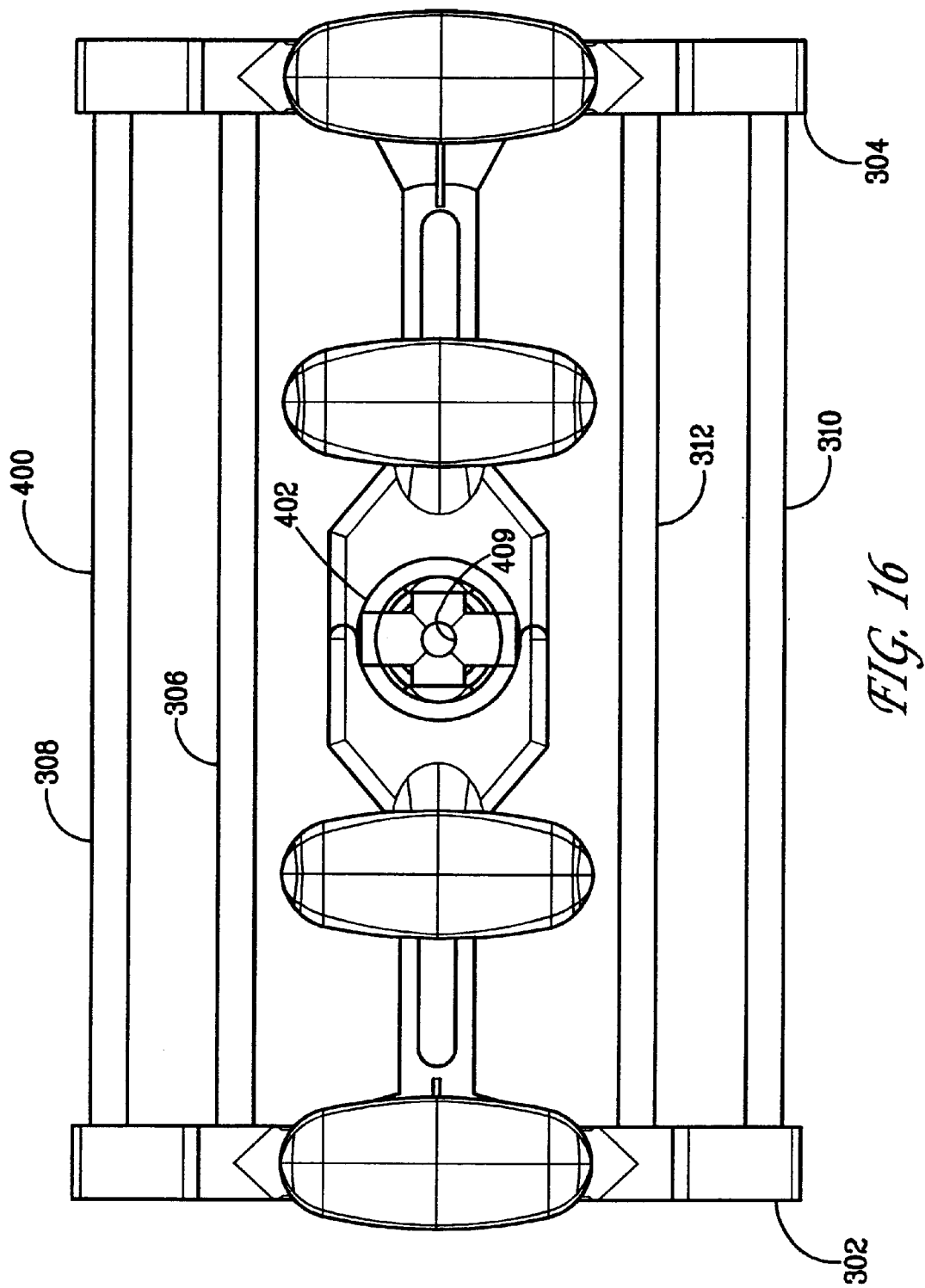
FIG. 16 is a plan view of the device of FIG. 15.
Figure 17:
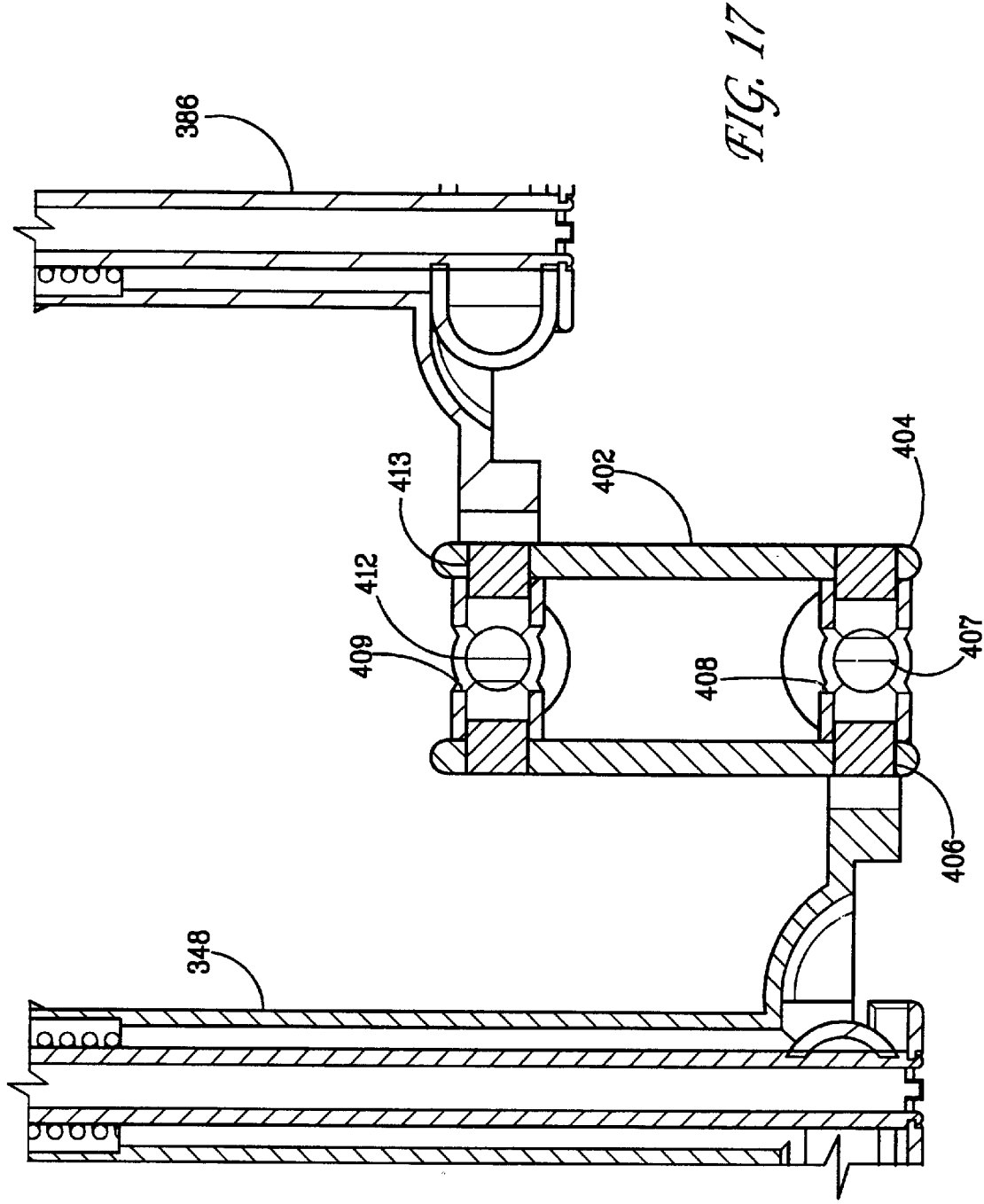
FIG. 17 is an enlarged fragmentary view of the U-joint.

FIGS. 15 through 17 illustrate targeting device 400, which represents another modification of targeting device 300. It employs a frame having end pieces 302 and 304 connected by rods 306, 308, 310 and 312 as in the embodiment of FIG. 13. The support structure is identical to that of the embodiment of FIG. 13. However, the targeting structure comprises a tubular U-joint housing 402 having a lower end 404 pivotally supporting a pivot pin 406. The ends of pin 406 are pivotally connected to a second pin 407 about an axis at right angles to the axis of pin 406. The ends of pin 407 are connected by arm means 408 to the lower end of locking tube 348. Housing 402 has a target opening 409 which passes through the pivot pin.

The upper end of housing 402 supports a pivot pin 412 which is pivotally connected to the lower end of locking tube 386 and a second pivot pin 413 so that the upper end of the U-joint housing can be swung toward and away from cross rod 314. This permits the viewing tube to be pivoted about the axis of the four pivot pins. When locked in position, the targeting device is then used for drilling the bone, and then inserting the fastener through opening 409 as previously described.

Figure 18:
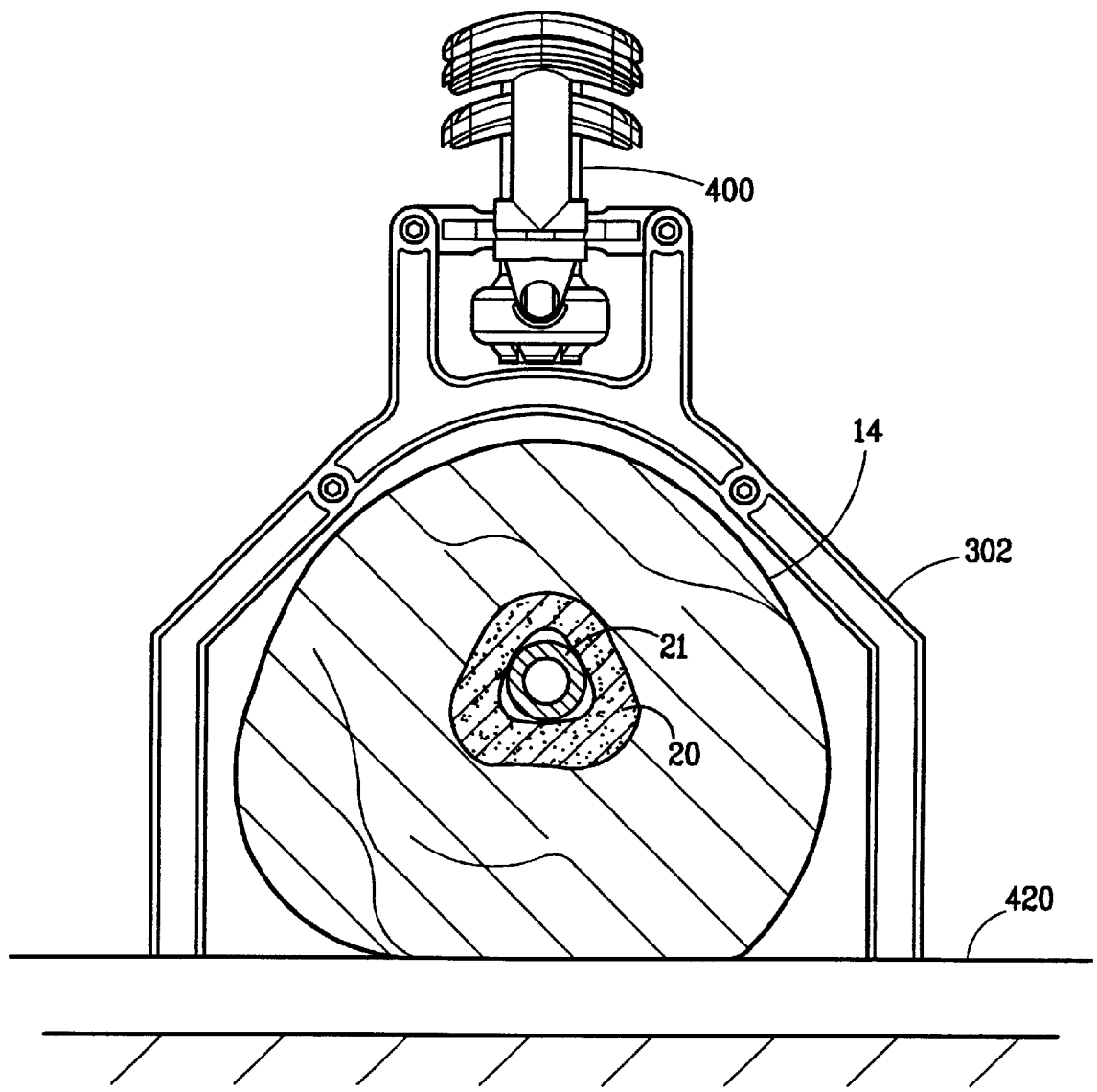
FIG. 18 is a sectional view showing how a preferred targeting device illustrating the invention can be mounted on a fixed surface rather than being strapped to the patient's limb.

FIG. 18 illustrates how targeting device 400 can be mounted on a relatively fixed surface 420 by modifying frame 302 so that it straddles the patient's leg 14 rather than being strapped to the leg.

Figure 19:
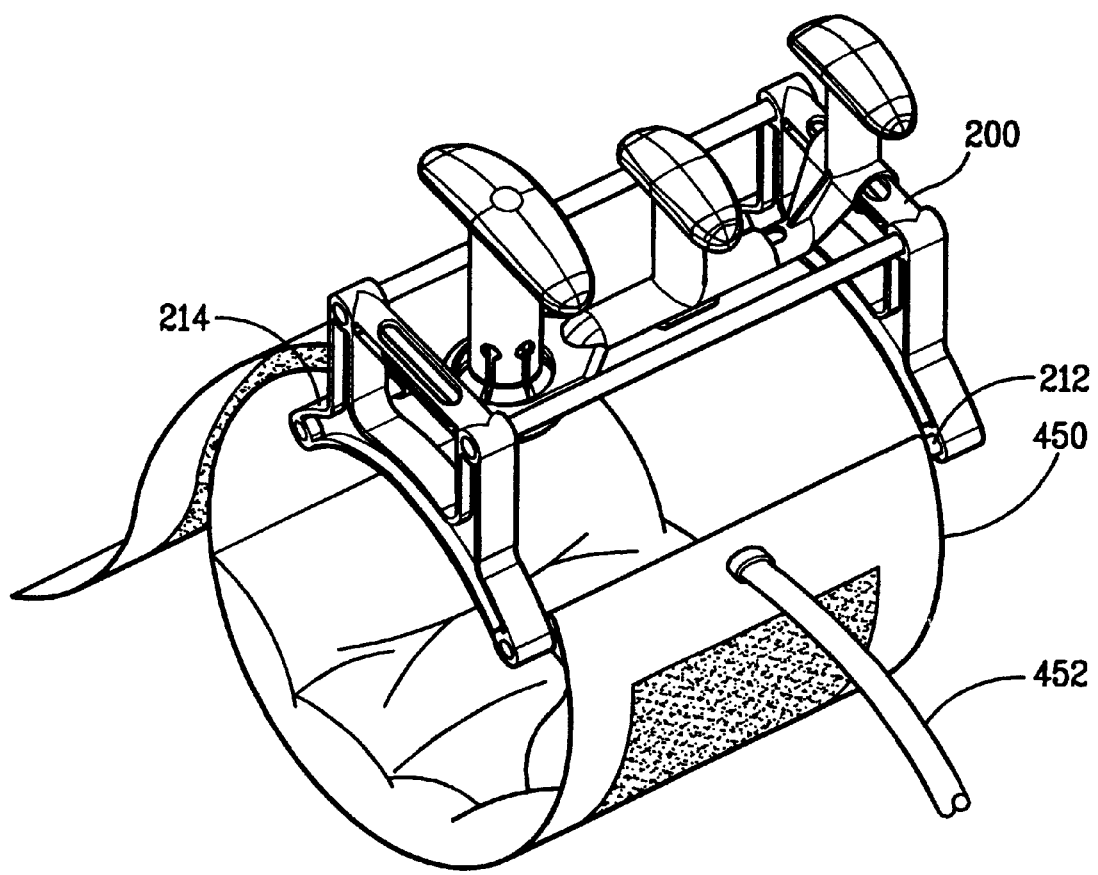
FIG. 19 is a view showing how a targeting device illustrating the invention can be strapped to the patient's limb employing an inflatable tourniquet.

FIG. 19 shows another method for mounting a targeting apparatus such as is illustrated in FIG. 7. In this case, an inflatable tourniquet 450 is wrapped around both the patient's leg and the two strapping rods and then inflated in the customary manner by delivering air through a tube 452 so that the targeting device is firmly anchored on the user's leg.

Figure 20:
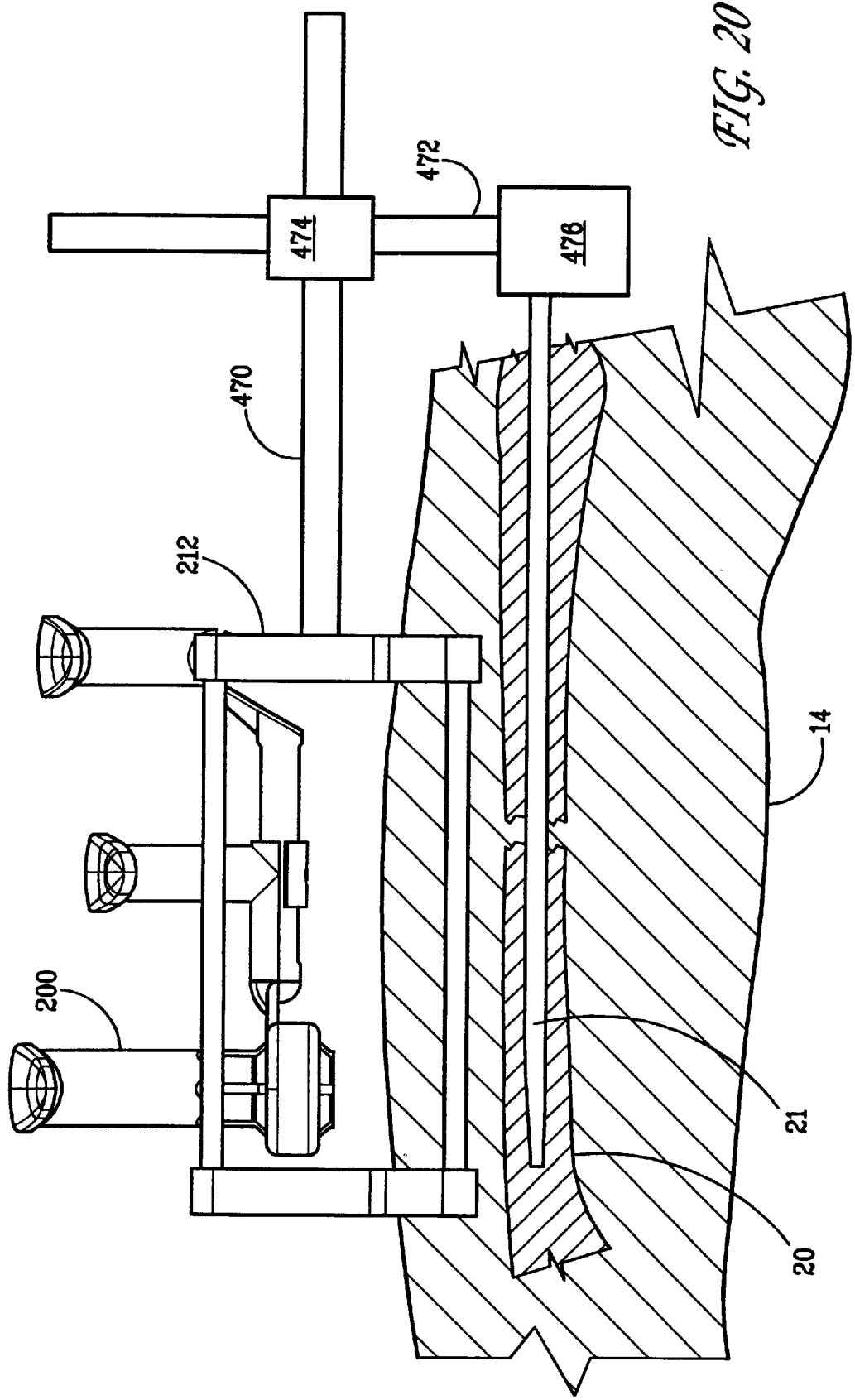
FIG. 20 is a view showing a targeting device illustrating the invention attached to a femoral nail.

FIG. 20 shows still another method for mounting the targeting device of FIG. 19. In this case the frame is attached by a support rod 470 which extends generally parallel to the femur and, in turn, is connected to a second support rod 472 by a suitable locking joint 474. Rod 472 is disposed at right angles to rod 470. The other end of the rod 472 carries a locking structure 476, which is attached to the nail so that the targeting device can be used to locate the locking holes.

Having described our invention, we claim:

1. A targeting apparatus for inserting a fastener into an implanted bone nail having a pair of locking openings aligned along an axis, comprising:
   a base adapted to be mounted in a fixed position with respect to a patient's limb having an implanted bone nail with a nail wall;
   a targeting device having a viewing axis;
   support structure mounted on the base for supporting the targeting device along the axis of a locking opening in the wall of the nail; including:
      first guide means on the support structure for supporting the targeting device for movement to an adjusted position in a first direction with respect to the nail;
      second guide means on the support structure for supporting the targeting device for movement in a direction generally at right angles to said first direction to a second adjusted position with respect to the nail such that the viewing axis of the targeting device generally intersects the axis of the locking opening;
   ball and socket means for supporting the targeting device on the base, the ball and socket means having a ball moveable in a socket to spherically adjust the targeting device to align the viewing axis of the targeting device with the axis of the locking opening in the nail for inserting a drill to form a hole in a bone in which the nail is implanted, and then to insert a fastener through the viewing axis of the targeting device for locking the bone to the nail.

2. A targeting apparatus as defined in claim 1, in which the first guide means comprises a rod disposed in a plane generally parallel to the axis of the nail, the viewing device being slidably mounted on the rod.

3. A targeting apparatus as defined in claim 1, in which the ball and socket means includes a targeting body having a pair of aligned spherical surfaces, and a viewing aperture passing along the spherical centers of the pair of aligned spherical openings.

4. A targeting apparatus for inserting a fastener into an implanted bone nail having a pair of locking openings aligned along an axis, comprising:
   a base adapted to be mounted in a fixed position with respect to an implanted bone nail with a nail wall;
   a targeting device having a viewing axis;
   support structure mounted on the base for supporting the targeting device along the axis of a pair of aligned openings in the wall of the nail; including:
      first guide means on the support structure for supporting the targeting device for movement to an adjusted position in a first direction with respect to the nail;
      second guide means on the support structure for supporting the targeting device for movement in a direction generally at right angles to said first direction to a second adjusted position with respect to the nail such that the viewing axis of the targeting device generally intersects the locking openings in the nail; and
   a ball and socket joint for supporting the targeting device on said base, the ball and socket joint being operative to spherically adjust the targeting device to align the viewing axis of the targeting device with the axis of the locking openings in the nail for inserting a drill to form a hole in a bone in which the nail is implanted, and then to insert a fastener through the viewing axis of the targeting device for locking the bone to the nail.

5. A targeting apparatus for targeting the axis of a blind hole in an implanted bone nail of a patient's limb, comprising:
   a frame;
   target means mounted on the frame including a viewing means capable of being moved co-axial to the axis of the blind hole, the targeting means includes a housing having and integral ball-shaped, slotted expandable join frictionally received in a socket so that a viewing axis in the targeting means can be spherically adjusted; and
   mounting means for mounting the frame in a fixed position relative to the blind hole comprising an inflatable tourniquet wrapped around the implant and the patient's limb and having ends connected to the frame.

6. A targeting apparatus for inserting a fastener into an implanted bone nail having a pair of locking openings aligned along an axis, comprising:
   a base adapted to be mounted in a fixed position with respect to a patient's limb having an implanted bone nail with locking openings;
   a targeting device mounted on the base having a viewing opening for receiving a drill that is aligned with the nail locking openings;
   ball and socket means for supporting the targeting device on the base, the ball and socket means having a ball moveable in a socket to spherically adjust the targeting device to align the viewing opening of the targeting device with an axis of the locking openings in the nail for inserting a drill to form a hole in a bone in which the nail is implanted, and then to insert a fastener through the viewing opening for locking the bone to the nail; and the viewing opening passing through the center of the ball.

7. A targeting apparatus as defined in claim 6, in which the ball comprises an elongated body having a longitudinal axis, the viewing opening passing along said longitudinal axis, and the ball being formed on a first end of the body, and a second ball formed at the opposite end of the body.

8. A targeting apparatus as defined in claim 1, in which the targeting device and the ball and socket means includes a housing having an integral ball-shaped, slotted expandable joint fictionally received in the socket so that the viewing axis can be spherically adjusted.

9. A targeting apparatus as defined in claim 8, in which the joint has an internally tapered opening.

10. A targeting apparatus as defined in claim 9, in which a clamping element having a externally tapered surface complementary to the internally tapered opening is received in an axial slot of the housing.

11. A targeting apparatus as defined in claim 4, in which the targeting device and the ball and socket joint includes a housing having an integral ball-shaped, slotted expandable joint fictionally received in a socket so that the viewing axis can be spherically adjusted.

12. A targeting apparatus as defined in claim 11, in which the joint has an internally tapered opening.

13. A targeting apparatus as defined in claim 12, in which a clamping element having a externally tapered surface complementary to the internally tapered opening is received in an axial slot of the housing.

14. A targeting apparatus as defined in claim 5, in which the joint has an internally tapered opening.

15. A targeting apparatus as defined in claim 14, in which a clamping element having a externally tapered surface complementary to the internally tapered opening is received in an axial slot of the housing.

16. A targeting apparatus as defined in claim 6, in which the targeting device and the ball and socket means includes a housing having an integral ball-shaped, slotted expandable joint frictionally received in the socket so that the viewing opening can be spherically adjusted.

17. A targeting apparatus as defined in claim 16, in which the joint has an internally tapered opening.

18. A targeting apparatus as defined in claim 17, in which a clamping element having a externally tapered surface complementary to the internally tapered opening is received in an axial slot of the housing.

* * * * *